United States Patent [19]

Barger et al.

[11] Patent Number: 4,857,666
[45] Date of Patent: * Aug. 15, 1989

[54] ALKYLATION/TRANSALKYLATION PROCESS

[75] Inventors: Paul T. Barger, Arlington Heights; Gregory J. Thompson, Waukegan; Raymond R. Herber, Medinah; Tamotsu Imai, Mt. Prospect, all of Ill.

[73] Assignee: UOP, Des Plaines, Ill.

[*] Notice: The portion of the term of this patent subsequent to Sep. 27, 2005 has been disclaimed.

[21] Appl. No.: 247,810

[22] Filed: Sep. 21, 1988

Related U.S. Application Data

[63] Continuation-in-part of Ser. No. 95,184, Sep. 11, 1987, Pat. No. 4,774,377.

[51] Int. Cl.[4] .................. C07C 1/00; C07C 2/68; C07C 5/22
[52] U.S. Cl. .................... 585/323; 585/466; 585/474; 585/475
[58] Field of Search .............. 585/323, 466, 474, 475; 502/31

[56] References Cited

U.S. PATENT DOCUMENTS

| 3,655,813 | 4/1972 | Kirsch et al. | 260/683.43 |
|---|---|---|---|
| 3,671,423 | 6/1972 | MacDonald et al. | 502/31 |
| 3,772,211 | 11/1973 | Mounce | 502/31 |
| 3,795,714 | 3/1974 | Pickert et al. | 260/683.43 |
| 3,851,004 | 11/1974 | Yang | 260/671 C |
| 4,550,090 | 10/1985 | Degman et al. | 502/31 |

Primary Examiner—Curtis R. Davis
Attorney, Agent, or Firm—Thomas K. McBride; John F. Spears, Jr.

[57] ABSTRACT

An alkylation-transalkylation process for the production of a monoalkylated aromatic compound is disclosed which maximizes the production of desirable monoalkylaromatic compounds, while limiting transalkylation catalyst deactivation. The process entails the combination of an alkylation reaction zone, a first seperation zone, a second separation zone, and a transalkylation reaction zone wherein the alkylation catalyst and transalkylation catalyst are dissimilar and where the alkylation catalyst is comprised of phosphoric acid material and the transalkylation catalyst is comprised of a crystalline aluminosilicate material. The transalkylation catalyst deactivation is reduced by transalkylating only dialkylated aromatic compounds. Additionally, the transalkylation catalyst is regenerable utilizing a hot liquid hydrocarbon wash.

13 Claims, 1 Drawing Sheet

ALKYLATION/TRANSALKYLATION PROCESS

CROSS-REFERENCE TO RELATED APPLICATION

This application is a continuation-in-part of prior copending application Ser. No. 095,184 filed Sept. 11, 1987, now U.S. Pat. No. 4,774,377 the contents of which are incorporated herein by reference thereto.

BACKGROUND OF THE INVENTION

The present invention is related to an improved alkylation/transalkylation process which utilizes a dual reactor system employing dissimilar catalysts to produce a monoalkylaromatic product. More specifically, this invention involves the use of a solid phosphoric acid catalyst to catalyze the alkylation reaction, and a regenerable inorganic oxide bound crystalline aluminosilicate material to catalyze the transalkylation reaction. The invention also relies upon a synergism of the two reaction zones and two separation zones to produce a high purify monoalkylated aromatic product in higher yields than those attainable with only an alkylation reaction zone.

The alkylation of aromatics with an alkylating agent in the presence of an alkylation catalyst is a process well known for its ability to produce such monoalkylaromatic products as ethylbenzene, cumene, linear alkylbenzenes and so forth. Such monoalkylaromatic compounds are important chemical precursors in the production of detergents and polymers among others. Alkylation catalysts that are known to produce alkylaromatic compounds include the well known Friedel-Crafts catalysts; sulfuric acid, phosphoric acid, hydrofluoric acid, and aluminum chloride in either liquid of solid supported form. Solid granular catalysts such as clays, zeolites, and amorphous materials have also been utilized as alkylation catalysts in both a modified and naturally occurring form.

The use of a transalkylation reaction zone in conjunction with an alkylation reaction zone for the production of monoalkylaromatics is also well known. A transalkylation reaction zone employed in a process in conjunction with an alkylation reaction zone enables the alkylation reaction zone to be operated at higher conversion conditions due to the ability of the transalkylation reactant to convert the undesired polyalkylaromatic compounds produced by the higher alkylation zone conversion conditions into desired monoalkylaromatic compounds. Transalkylation catalysts that are known to have utility in the production of alkylaromatics from polyalkylaromatics include Friedel-Crafts catalyst such as sulfuric acid, phosphoric acid, aluminum chloride in either the liquid or solid supported form, and the like. Solid granular catalysts such as clays, zeolites, and amorphous materials have also been utilized as transalkylation catalysts.

A myriad of processing schemes employing an alkylation reaction zone, a transalkylation reaction zone, and a separation zone, and employing various product, feed, and intermediate product recycles are well known to produce monoalkylaromatic products. One drawback concerning known alkylation/transalkylation processes is the sometimes rapid deactivation of the transalkylation catalyst due to the presence of trialkylaromatic and higher boiling compounds in the transalkylation reaction zone feed. This rapid deactivation requires that frequent catalyst regenerations be performed, or that the transalkylation catalyst be frequently replaced. The replacement or frequent regeneration of a deactivated transalkylation catalyst can therefore become time-consuming and costly.

A drawback inherent to existing alkylation processes which utilize a Friedel-Crafts catalyst such as solid phosphoric acid or hydrofluoric acid as the alkylation catalyst is that many of these catalysts require a water cofeed and produce an extremely corrosive sludge by-product. The utilization of such high activity, sludge-producing catalysts in an alkylation process necessitates the operation of the process at high conversion once-through conditions which tend to produce greater amounts of unwanted di- and trialkylaromatics. The addition of a transalkylation reaction zone containing a stable, active transalkylation catalyst to such an alkylation process enables the conversion of the dialkylaromatics to monoalkylaromatics at high conversions without detrimentally affecting transalkylation catalyst life.

INFORMATION DISCLOSURE

Prior alkylation art discloses many different catalysts and process configurations employing alkylation and transalkylation reaction zones for the production of monoalkylated aromatics. The use of phosphoric acid catalysts and the use of crystalline aluminosilicates as alkylation and/or transalkylation catalyst is well known.

A great many of the prior art cases describing an alkylation/transalkylation process specify the use of the same catalyst in both reaction zones. This is the case in U.S. Pat. No. 4,459,426 (Inwood et al) which describes a process that has a configuration similar to the configuration of the present invention except that, among other differences, it clearly dictates the use of a steam stabilized hydrogen Y-zeolite as the alkylation and transalkylation reaction zone catalyst. U.S. Pat. No. 3,751,504 (Keown et al) discloses the use of a crystalline aluminosilicate catalyst in both the alkylation and transalkylation reaction zones of an aromatic alkylation process. The process configuration disclosed and the fact that the process disclosed utilizes a gas phase reaction are some of the areas where this invention differs from the present invention.

Fewer prior art disclosures teach the merits of using dissimilar catalysts in the alkylation and transalkylation zones of an aromatic alkylation process. One in particular, U.S. Pat. No. 3,551,510 (Pollitzer et al), teaches of the use of a solid phosphoric acid catalyst in the alkylation zone, and of the use of a hot hydrochloric acid extracted mordenite catalyst in the transalkylation zone. The '510 patent describes an alkylation process very similar to that of the instant invention. However, the process described in the '510 patent can be distinguished on a process basis. The process described in the '510 patent finds the transalkylation reactor immediately after the alkylation reactor with no separation of the alkylation reaction zone products between. Thus, the entire alkylation reaction zone products are exposed to the transalkylation catalyst at transalkylation conditions. According to the instant process, this is an undesirable flow scheme as the heavy alkylation zone products comprising trialkylaromatics and heavier components would accelerate the transalkylation catalyst deactivation. Additionally, by accepting the entire alkylation reaction zone product stream, the transalkylation reactor of the '510 patent would likely be much larger in size than that of the present invention in order to maintain similar conversions, thus increasing process cost.

U.S. Pat. No. 4,008,290 teaches the use of a solid phosphoric acid alkylation catalyst in a process containing a transalkylation reaction zone that is similar to, but not the same as, that of the instant invention. The process disclosed in U.S. Pat. No. 4,008,290 differs from that of the instant invention in that, among other items, it teaches of the use of an alkylation reaction zone effluent recycle stream to the inlet of the alkylation reaction zone for the purpose of temperature and conversion control. The process of the instant application teaches away from the use of a direct alkylation reaction zone product recycle as the recycled material contains an acid sludge component produced by the interaction of water with the solid phosphoric acid. The acid sludge in the recycle stream detrimentally affects alkylation catalyst life and also is corrosive to typical process metallurgy. In an additional distinguishing feature, it is an aspect of the present invention that the feed to the transalkylation reaction zone be comprised essentially of dialkylaromatics and the aromatic substrate in order to maximize the useful life of the transalkylation catalyst while increasing overall process conversion. A second separation zone is employed in the instant process to provide a high purity dialkylaromatic fraction. The '290 patent however utilizes the entire heavy alkylate stream containing di-, tri-, and polyalkylated aromatics and recovered in a single separation zone as the transalkylation reaction zone feed. The inclusion of components heavier than dialkylaromatics in the transalkylation reaction zone feed has been found to cause detrimental accelerated deactivation of the transalkylation catalyst.

The use of a zeolitic or crystalline aluminosilicate catalyst for transalkylation is described in various prior art disclosures. U.S. Pat. No. 3,562,345 (Mitsche) discloses the use of a crystalline aluminosillicate material as a transalkylation catalyst characterized in that the material has a pore diameter of from 3 to 8 angstroms, and a $SiO_2/Al_2O_3$ mole ratio of from 6 to 12, where the crystalline aluminosilicate material is mordenite. The disclosure is however silent to the benefits of utilizing such a catalyst in conjunction with an alkylation reaction zone such as in the process of the instant invention.

Regeneration of alkylation or transalkylation catalysts has been recognized as a viable means of maintaining catalyst activity over a long period of time. U.S. Pat. No. 3,851,004 discloses the regeneration of an alkylation catalyst comprising a metal-modified zeolite by contacting the catalyst at a temperature of from 27° to 300° C. with a $C_4$–$C_{12}$ hydrocarbon saturated with hydrogen. U.S. Pat. No. 3,795,714 discloses a method of regenerating a catalyst with an inert saturated hydrocarbon solvent. Finally, U.S. Pat. No. 3,655,813 describes an alkylation process including a gas phase step for regenerating the catalyst by exposing it to an inert gas, an inert sorbate, or mixtures thereof.

The unique process combination disclosed in the present invention has surprisingly been found to have great utility in the production of a monoalkylaromatic compound from a feed comprising an aromatic compound and an alkylating agent where the desired monoalkylaromatic product is produced in high yields in a process characterized as being efficient and containing catalysts with extended useful lives.

OBJECTS AND EMBODIMENTS

A new process which employs an alkylation reaction zone, a first and second separation zone, and a transalkylation reaction zone, and which utilizes a solid phosphoric acid alkylation catalyst and a regenerable crystalline aluminosillicate transalkylation catalyst has been surprisingly found to have utility in producing a monoalkylaromatic compound in very high yields. Additionally, it has been discovered that separating the dialkylaromatics from a portion of the undesired hexylbenzene product and virtually all of the trialkylaromatic and higher boiling products prior to transalkylation of the dialkylaromatics enables the process to be run much more efficiently with an added benefit in that the transalkylation catalyst life is increased. Finally, the transalkylation catalyst that has been surprisingly found to produce the best results in the above alkylation/transalkylation process possesses the additional advantage of being regenerable by washing the catalyst with hot liquid hydrocarbons.

In one of its broad aspects, the present invention embodies an improved alkylation/transalkylation process which comprises a unique combination of an alkylation reaction zone containing an alkylation catalyst comprising a solid phosphoric acid component, a first separation section, a second separation section, and a transalkylation reaction zone containing a regenerable crystalline aluminosilicate transalkylation catalyst wherein an alkylating agent and an aromatic substrate are reacted to produce a monoalkylaromatic product. The first separation section is characterized in that it separates as fractions; (1) the unreacted aromatic substrate for use as a portion of the alkylation reaction zone and/or transalkylation reaction zone feed, (2) compounds with boiling points higher than that of the desired monoalkylated aromatic compound including di- and trialkylated aromatics, and (3) a monoalkylaromatic compound which is recovered as the desired product. An undesired product stream comprising hydrocarbon compounds that are lower in molecular weight than the aromatic substrate is also recovered in the first separation section. The second separation section is characterized in that it accepts as feed the fraction from the first separation zone comprising compounds with boiling points higher than that of the desired monoalkylated aromatic and separates from this stream a dialkylated aromatic-rich fraction, and fractions with boiling points above and below that of the dialkylated aromatic-rich fraction.

It is a further objective of this invention to utilize as the alkylation reaction zone catalyst a solid phosphoric acid catalyst, and to use as the regenerable transalkylation reaction zone catalyst, an inorganic oxide bound crystalline aluminosillicate catalyst. Additionally, it should be noted that the alkylating agent employed in the process can consist of an alkene, an alcohol, an alkylhalide, an alkylsulfonate, or mixtures thereof where the carbon number of the alkylating agent ranges from 2–18.

The transalkylation catalyst is regenerated by halting the flow of the separated dialkylaromatic-rich hydrocarbon fraction of the second separation zone to the transalkylation reaction zone. This allows only the aromatic substrate feed to the transalkylation reaction zone to contact the transalkylation catalyst. The aromatic substrate contacts the transalkylation catalyst in the liquid phase at elevated temperature until essentially no catalyst deactivating material remains on the catalyst. After the aromatic substrate contacting step is complete, the flow of the separated dialkylated aromatic-rich hydrocarbon fraction to the transalkylation reaction zone is resumed.

In a more specific embodiment, this invention relates to a process for the production of isopropylbenzene hereinafter referred to as cumene from the alkylation reaction of the aromatic substrate benzene with the alkylating agent propylene. The alkylation reaction takes place in an alkylation reaction zone containing a solid catalyst comprised of a phosphoric acid component where the catalyst exists as spheres, extrudates, or granular particles. The alkylation reaction zone is further characterized by its ability to accept as a feed a recycled portion of the unreacted aromatic substrate which has been recovered in the first separation zone. Liquid fractions comprising all of the alkylation reaction zone product stream and the entire transalkylation reaction zone product stream are directed to the first separation zone for separation into fractions comprising a benzene-rich fraction, a cumene-rich fraction, and a fraction rich in compounds with boiling points higher than cumene. The liquid fraction rich in compounds with boiling points higher than cumene which is recovered in the first separation zone is subsequently directed to the second separation zone where it is separated into a diisopropylbenzene-rich fraction, and fractions rich in components with boiling points above and below that of the diisopropylbenzene-rich fraction. The transalkylation reaction zone contains a regenerable crystalline aluminosilicate catalyst in the form of spheres, extrudates, or granular particles. The transalkylation reaction zone catalyst is preferably mordenite, bound with from 5% to 95% by weight of an inorganic oxide support selected from the group consisting of $Al_2O_3$, $SiO_2$, $AlPO_4$, andmixtures thereof. In addition, the crystalline aluminosilicate transalkylation catalyst may be modified by stream stabilization, acid modification, ion exchange, and similar methods. The transalkylation zone feed is comprised of a portion of the separated unreacted benzene fraction and the diisopropylbenzene-rich fraction of which a portion to all of the unreacted benzene fraction has been recovered in the separation section. The transalkylation catalyst is regenerated when the diisopropylbenzene conversion across the transalkylation catalyst is at least 25 percent below that of the fresh catalyst diisopropylbenzene conversion performance. The transalkylation catalyst is regenerated by directing the flow of the diisopropylbenzene-rich fraction of the second separation zone to the inlet of the alkylation reaction zone. The transalkylation catalyst is then contacted with the first portion of the separated benzene-rich fraction in the liquid phase and at a temperature of at least 250° C. until essentially no catalyst reactivating material remains on the transalkylation catalyst. Finally, the flow of the diisopropylbenzene-rich fraction of the second separation zone is directed back to the transalkylation reaction zone. These, as well as other embodiments of the present invention will become evident from the following, more detailed description.

BRIEF DESCRIPTION OF THE DRAWING

Figure 1:
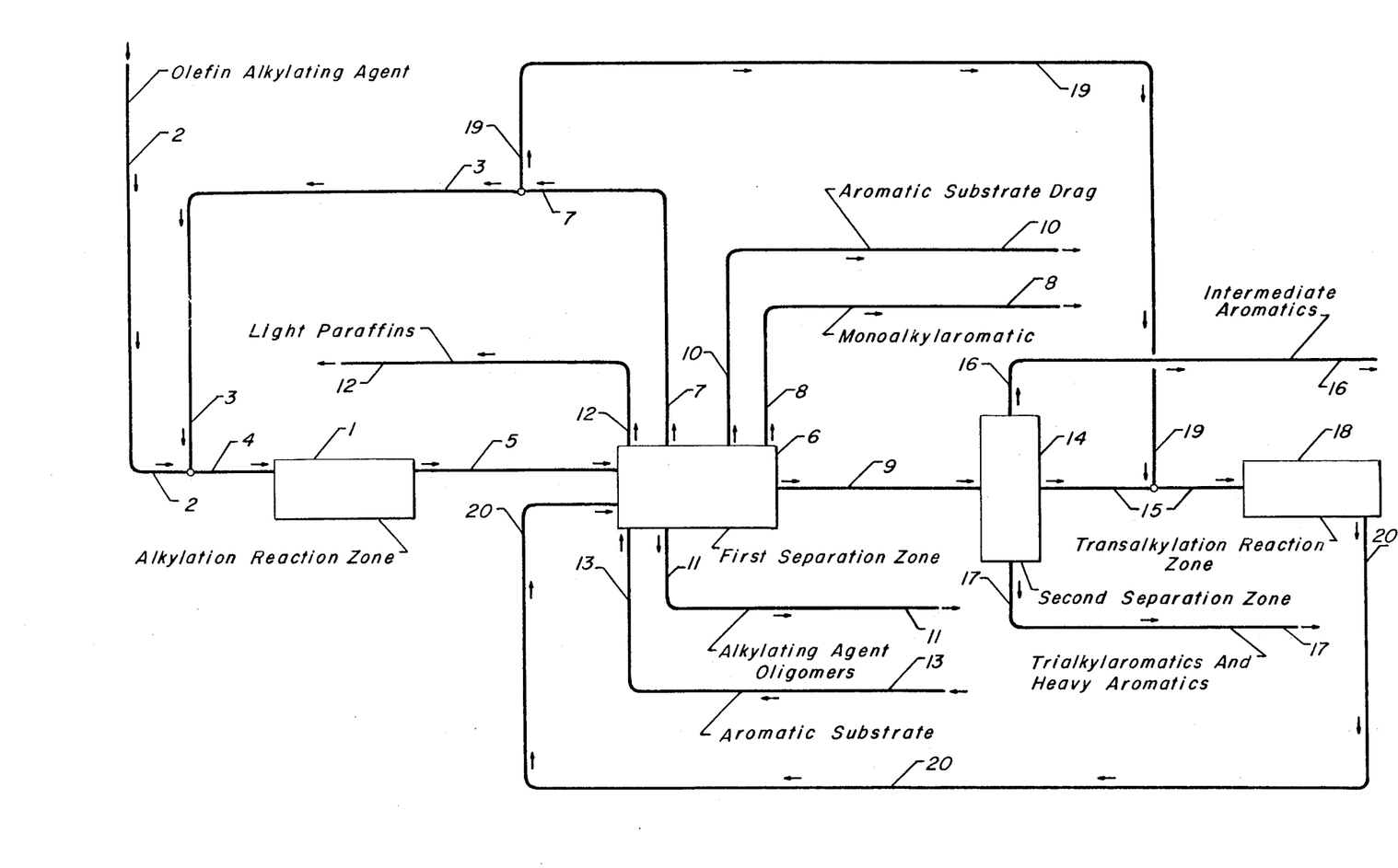

Understanding of this invention will be facilitated by reference to the Figure which is a diagram of the process flow scheme of the instant invention. The description will be directed toward the production of cumene from benzene and propylene to provide clarity to the description. However, the description is not intended to limit the scope of the invention in any way. As stated hereinabove, the first step of the process of the present invention comprises passing a mixed feed stream 4 into an alkylation reaction zone 1 containing an alkylation catalyst, wherein the mixed feed stream 4 is comprised of a benzene aromatic substrate feed stream 3, and a propylene olefin alkylating agent feed stream 2. The alkylation reaction zone product stream 5 is then sent to the first separation zone 6.

The first separation zone 6 accepts as feed all of the alkylation reaction zone product stream 5 and the entire transalkylation reaction zone product stream 20. In addition, a portion of all of the benzene aromatic substrate used as alkylation and transalkylation reaction zone feed may be initially introduced into the first separation zone 6 via stream 13 for purification of the aromatic substrate feed. The first separation zone 6 produces at least four product streams 8, 10, 11, and 12 and two intermediate streams 7 and 9. The products separated in the first separation zone 6 include the desired cumene monoalkylaromatic stream 8, an alkylating agent oligomer stream 11, a light paraffin byproduct stream 12, and a benzene aromatic substrate rich drag stream 10. The intermediate streams recovered in the first separation zone are a benzene-rich aromatic substrate stream 7 which can be employed as a portion to all of the benzene aromatic substrate feed stream 3 to the alkylation reaction zone. Additionally, the recovered benzene-rich aromatic substrate stream 7 can be used as a portion to all of the transalkylation reaction zone benzene aromatic substrate feed via line 19. Components with boiling points higher than that of the desired cumene monoalkylaromatic compound are recovered in the first separation zone 6 and sent in entirety via stream 9 to the second separation zone 14.

The second separation zone 14 accepts as feed, stream 9 containing the components with boiling points higher than the desired cumene monoalkylaromatic component. The second separation zone produces at least two product streams, 16 and 17, and one intermediate stream 15. The product streams from the second separation zone 14 include an intermediate aromatic product stream 16 comprised of hydrocarbons with boiling points lower than that of the desired diisopropylbenzene dialkylaromatic-rich stream 15, and product stream 17 comprising hydrocarbons with boiling points higher than that of the diisopropylbenzene dialkylaromatic-rich stream 15. The intermediate stream 15 produced by the second separation zone 14 comprises diisopropylbenzene dialkylaromatic compounds and small amounts of aromatic components with a similar boiling point and is directed to the transalkylation reaction zone 18.

The transalkylation reaction zone 18 accepts as feed the diisopropylbenzene dialkylated aromatic compounds recovered in the second separation zone 14 and supplied to the transalkylation reaction zone 18 via stream 15. A benzene aromatic substrate utilized as an alkylation reaction zone feedstock is also employed as a transalkylation reaction zone 18 feedstock. The aromatic substrate can be supplied directly to the reactor from a source outside of the process, or as a recycle stream of aromatic substrate recovered in the separation zone via stream 19 or as a mixture of both.

DETAILED DESCRIPTION

It is the object of the present invention to provide a new process for the production of monoalkylated aromatics in high yields wherein the desired product is produced through the synergism of an alkylation reaction zone containing an alkylation reaction catalyst, a transalkylation reaction zone containing a transalkylation catalyst and two separation zones which unite the two reaction zones to create a continuous integrated process.

The first step of the process of the present invention comprises passing to an alkylation reaction zone containing an alkylation catalyst an admixture of an alkylating agent and an aromatic substrate. The alkylating agent which may be charged to the alkylation reaction zone may be selected from a group of diverse materials including monoolefins, diolefins, polyolefins, acetylenic hydrocarbons, and also alkylhalides, alcohols, ethers, esters, the later including the alkylsulfates, alkylphosphates and various esters of carboxylic acids. The preferred olefin-acting compounds are olefinic hydrocarbons which comprise monoolefins containing one double bond per molecule. Monoolefins which may be utilized as olefin-acting compounds in the process of the present invention are either normally gaseous or normally liquid and include ethylene, propylene, 1-butene, 2-butene, isobutylene, and the higher molecular weight normally liquid olefins such as the various pentenes, hexenes, heptenes, octenes, and mixtures thereof, and still higher molecular weight liquid olefins, the latter including various olefin polymers having from about 9 to about 18 carbon atoms per molecule including propylene trimer, propylene tetramer, propylene pentamer, etc. Cycloolefins such as cyclopentene, methylcyclopentene, cyclohexene, methylcyclohexene, etc., may also be utilized, although not necessarily with equivalent results. Other hydrocarbons such as paraffins, naphthenes and the like containing 2 to 18 carbon atoms may also be present in the alkylating agent.

It is a preferred embodiment of the present invention that the monoolefin contains at least 2 and not more than 14 carbon atoms. More specifically, it is preferred that the monoolefin is propylene.

The aromatic substrate of the present invention which is charged to the alkylation reaction zone in admixture with the alkylating agent may be selected from a group of aromatic compounds which include individually and in admixture, benzene, and monocyclic alkyl-substituted benzene of from 7 to 12 carbon atoms having the structure where R is methyl, ethyl or a combination thereof, and n is an integer from 1 to 5. In other words, the aromatic substrate portion of the feedstock may be benzene, an alkylaromatic containing from 1 to 5 methyl and/or ethyl group substituents, and mixtures thereof. Non-limiting examples of such feedstock compounds include benzene, toluene, xylene, ethylbenzene, mesitylene (1,3,5-trimethylbenzene) and mixtures thereof. It is specifically preferred that the aromatic substrate is benzene.

The alkylation reaction zone contains an alkylation catalyst. A particularly preferred alkylation catalyst comprises a solid phosphoric acid-containing composite. The phosphoric acid-containing composite may be made by combining an acid of phosphorus such as pyro-, or tetraphosphoric acid with the solid support. It is not intended to infer that the different acid of phosphorus which may be employed will produce catalysts which have identical effects upon any given alkylation reaction as each of the catalyst produced from different acids and by slightly varying procedures will exert its own characteristic action.

Triphosphoric acid, which may be represented by the formula $H_5P_3O_{10}$, may also be used as one of the starting materials for the preparation of the phosphoric acid-containing composite utilized in the alkylation reaction zone of this invention.

A phosphoric acid mixture which is generally referred to as polyphosphoric acid may also be employed in manufacturing the composite. Polyphosphoric acid is formed by heating orthophosphoric acid or pyrophosphoric acid or mixtures thereof in suitable equipment such as carbon lined trays heated by flue acids or other suitable means to produce a phosphoric acid mixture generally analyzing from about 79% to about 85% by weight $P_2O_5$.

Tetraphosphoric acid, having the general formula $H_6P_4O_{13}$ which corresponds to the double oxide formula $3H_2O.2P_2O_5$ may be considered as the acid resulting when three molecules of water are lost by four molecules of orthophosphoric acid, $H_3PO_4$. The tetraphosphoric acid may be manufactured by gradual or controlled dehydration or heating of orthophosphoric acid and pyrophosphoric acid or by adding phosphorus pentoxide to those acids in proper amounts.

The phosphoric acid-containing composite may comprise a high surface area solid support. By the term "high surface area" is meant a surface area measured by surface adsorption techniques within a range of about 25 to about 500 or more $m^2/g$ and preferably a support having a surface area of approximately 100 to 300 $m^2/g$. Therefore, satisfactory supports for the preparation of catalysts for use in the process of this invention include high surface area crystalline alumina modifications such as gamma-, eta-, and theta-alumina, although these are not necessarily of equivalent suitability. In addition to the aforementioned gamma-, eta-, and theta-aluminas which may be utilized as solid supports, it is also contemplated that other refractory oxides, and mixtures thereof, such as silica, zirconia, magnesia, thoria, etc., silica-alumina, silica-magnesia, alumina-silica-magnesia, alumina-thoria, alumina-zirconia, etc. may also be utilized as solid supports for the alkylation catalyst of the process of the present invention.

The phosphoric acid-containing composite utilized in alkylation reaction zone 2 may contain from about 8% or lower to about 80% or higher, by weight, of phosphoric acid, and preferably from about 10% to about 75% by weight of phosphoric acid.

In addition to the solid phosphoric acid alkylation catalyst which may be utilized in the alkylation reaction zone, it is also contemplated that other alkylation catalysts such as a boron halide-modified refractory inorganic oxide catalyst as well as the various crystalline aluminosilicate alkylation catalysts may also be utilized in the instant alkylation-transalkylation process.

In a continuous process for alkylating aromatic hydrocarbons with olefins, the previously described reactants are continuously fed into a pressure vessel containing preferably the above described solid phosphoric acid catalyst. The feed admixture may be introduced into the alkylation reaction zone containing the alkylation catalyst at a constant rate, or alternatively, at a variable rate. Normally, the aromatic substrate and olefinic alkylating agent are contacted at a molar ratio of from about 1:1 to 20:1 and preferably from about 2:1 to 8:1. The preferred molar feed ratios help to maximize the catalyst life cycle by minimizing the deactivation of the catalyst by coke and heavy material deposition upon the catalyst. The catalyst may be contained in one bed within a reactor vessel or divided up among a plurality of beds within a reactor. The alkylation reaction system may contain one or more reaction vessels in series. The feed to the reaction zone can flow vertically upwards, or downwards through the catalyst bed in a typical plug flow reactor, or horizontally across the catalyst bed in a radial flow type reactor.

In some cases, in order to maintain the reaction temperature in the preferred range and thus reduce the formation of unwanted polyalkylaromatics, it may be desirable to quench the reactants to dissipate heat of reaction. A quench stream comprised of the alkylating agent olefin, or a portion of the acidic syrup-free monoalkylaromatic, or aromatic substrate recovered in the first separation zone, or mixtures thereof may be injected into the alkylation reactor system in order to dissipate heat and supply additional amounts of olefin alkylating agent and unreacted aromatic substrate at various locations within the reaction zone. This is accomplished for example in a single-stage reactor by multiple injection of the aforementioned quench steam components into the reaction zone via strategically placed inlet lines leading into said reaction zone. The amount and composition of quench material injected into either a single stage reaction system or multi-stage reaction system may be varied according to need. Benefits resulting from multiple quench injection include elimination of costly cooling apparatus in the process, improved selectivity to formation of the desired alkylaromatic compound, provision for a larger heat sink and optimization of the olefin to aromatic compound molar ratio throughout the reaction zone thus resulting in increased yield of the desired monoalkylated aromatic compound.

Temperatures which are suitable for use in the process herein are those temperatures which initiate a reaction between an aromatic substrate and the particular olefin used to selectively produce the desired monoalkylaromatic compound. Generally, temperatures suitable for use are from about 100° C. to about 390° C., especially from about 150° C. to about 275° C. Pressures which are suitable for use herein preferably are above about 1 atm but should not be in excess of about 130 atm. An especially desirable pressure range is from about 10 to about 40 atm; with a liquid hourly space velocity (LHSV) based upon the benzene feed rate of from about 0.5 to about 50 hr$^{-1}$, and especially from about 1 to about 10 hr$^{-1}$. It should be noted that the temperature and pressure combination used herein is to be such that the alkylation and transalkylation reactions take place in essentially the liquid phase. In a liquid phase process for producing alkylaromatics, the catalyst is continuously washed with reactants, thus preventing buildup of coke precursors on the catalyst. This results in reduced amounts of carbon forming on said catalyst in which case catalyst cycle life is extended as compared to a gas phase alkylation process in which coke formation and catalyst deactivation is a major problem. To further reduce the rate of catalyst deactivation, it is contemplated that H$_2$ may be added to the alkylation reaction zone feed and the transalkylation reaction zone feed in an amount sufficient to saturate the respective reaction zone liquid feeds. The addition of H$_2$ in equilibrium amounts to the respective liquid phase feed streams helps to reduce the catalyst deactivation rate by inhibiting the polymerization potential of pore blocking polymerizable compounds produced by the process.

Additionally, a regulated amount of water is preferably added to the alkylation reaction zone. In order to substantially prevent loss of water from the catalyst and subsequent decrease in catalyst activities, an amount of water or water vapor such as steam is added to the charge so as to substantially balance the vapor pressure of the alkylation catalyst hereinabove described. This amount of water varies from about 0.01 to 6% by volume of the organic material charged to the alkylation reaction zone. The water is then typically removed with the light by-product stream recovered in the first separation zone.

A substantial portion of the aromatic substrate hydrocarbon and essentially all of the olefin alkylating agent react in the alkylation reaction zone in the presence of the solid phosphoric acid catalyst to form, in addition to the desired monoalkylaromatic compound, undesired polyalkylaromatic compounds, and undesired monoalkylaromatic compounds. The undesirable polyalkylaromatic hydrocarbons typically contain two or more alkyl groups that have from 1 to 18 carbon atoms, for example, the di-, tri-, and tetraisopropylbenzene hydrocarbons. The undesired monoalkylaromatics typically contain alkyl groups that have carbon numbers greater or less than that of the alkyl compound of the desired monoalkylaromatic.

Additionally, where an alkylaromatic with an unsaturated alkyl side chain is the desired monoalkylaromatic product, then an undesired monoalkylaromatic compound might also comprise a monoalkylaromatic containing saturated alkyl side chains of the same carbon number as the desired unsaturated alkyl side chains. It is an important aspect of this invention to recover and transalkylate dialkylaromatic compounds in order to maximize the amount of the desired monoalkylaromatic hydrocarbons produced by the process while minimizing transalkylation catalyst deactivation.

The alkylation reaction zone product is directed in entirety to the first separation zone. In the first separation zone, the alkylation reaction zone product is separated into at least three fractions using any conventional separation techniques available that will result in essentially pure fractions of (1) an aromatic substrate, (2) a monoalkylaromatic compound, and (3) compounds with boiling points higher than that of the desired monoalkylaromatic compound. The first separation zone fraction comprising compounds with boiling points higher than that of the desired monoalkylaromatic compound is then directed to the second separation zone. In the second separation zone, the feed comprising compounds with boiling points higher than the desired monoalkylaromatic is separated using any conventional separation techniques available that will result in the recovery of a dialkylaromatic-rich fraction and fractions with boiling points above and below that of the dialkylaromatic-rich fraction.

The recovery and removal of the trialkylaromatic and higher boiling compounds from the process in the second separation zone as the fraction with a boiling point above that of the dialkylaromatic-rich fraction before their introduction into the transalkylation reaction zone succeeds in eliminating compounds from the potential transalkylation reaction zone feed which might otherwise accelerate transalkylation catalyst deactivation. As previously mentioned, an intermediate fraction containing components with boiling points lower than that of the dialkylaromatic-rich fraction is also recovered in the second fractionation zone. Intermediate fraction components typically are alkylaromatics with short saturated side chains such as methylbenzene, ethylbenzene, butylbenzene, propylbenzene, and the like. The recovery and removal of the intermediate aromatic compounds from the process before their introduction into the transalkylation reaction zone succeeds in reducing the amount of components from the process which might otherwise be converted into detrimental products in the transalkylation reaction zone which would eventually accumulate in the process as a refractory product diluent. Such diluents are typically removed from the process as undesired product contaminants or as part of a useless drag stream of a desired intermediate component such as an aromatic substrate drag stream. The diluents must be removed from the process in order to prevent their accumulation in the process. By removing most potential diluents in the second separation zone, the process is improved as desired product purity is improved and drag stream rates are reduced.

An example of some of the separation techniques that can be employed alone or in combination in the first or second separation zones to produce essentially pure fractions of the hereinbefore mentioned separation zone products are: distillation including vacuum, atmospheric, and superatmospheric distillation; extraction techniques including, for example, liquid/liquid extractions, vapor/liquid extractions, supercritical extractions and others; absorption techniques, adsorption techniques, and any other known mass transfer techniques which can achieve the recovery of the desired first and second separation zone products in essentially pure fractions. The separation processes mentioned above are included as examples of the many techniques which could be utilized to achieve the necessary separation, purification and recovery of the alkylation and transalkylation reaction zone products. Hence, separation zone processing conditions are not disclosed as they will depend upon the choice of the separation techniques employed and further upon the configuration of the separation zone equipment. It is expected that continuous distillation will be the primary separation technique used in the separation zones. The optimal distillation conditions will again depend upon the exact scheme chosen to achieve the desired separation.

As previously mentioned, the transalkylation reaction zone product as will hereinafter be described is directed as a whole to the first separation zone. Additionally, a portion to all of the fresh aromatic substrate feed stream may be directed initially to the first separation zone. Directing the aromatic substrate feed to the first separation zone enables the processing of aromatic substrate feedstocks which are comprised mainly of the desired aromatic substrate feed component but which may contain deleterious amounts of undesirable components. In directing the aromatic substrate feedstock to the first separation section, an essentially pure aromatic substrate feed stream can be provided as a portion to all of the feedstock to both the alkylation reaction zone and transalkylation reaction zone from a previously contaminated or diluted aromatic substrate feedstock.

To reiterate, the first separation zone product fractions are essentially pure streams of the desired monoalkylaromatic compound, the unreacted aromatic substrate feed compound, and compounds with boiling points higher than that of the desired monoalkylaromatic compound. In addition, a first separation zone product fraction comprised of hydrocarbon materials lower in molecular weight than the aromatic substrate feed compound is separated in the first separation zone and recovered from the process as an undesirable product of the alkylation zone and transalkylation zone reactions. Other undesirable by-product fractions which may be separated from the alkylation and transalkylation reaction products in the first separation zone include a benzene drag stream, and propylene oligomers. The second separation zone produces a dialkylaromatic-rich fraction, and fractions with boiling points higher and lower than that of the desired dialkylaromatic-rich fraction. The second separation zone fraction comprising hydrocarbons with lower boiling points than the desired dialkylated aromatic-rich fraction will normally comprise undesirable saturated alkylaromatic compounds, while the said heavier boiling fraction will typically be rich in trialkylaromatic and higher boiling hydrocarbons. Fractions comprising the desired monoalkylaromatic product, the light hydrocarbon by-product materials, the benzene drag stream, propylene oligomers, and the hydrocarbons with boiling points higher and lower than the desired dialkylaromatic-rich fraction exit the process and are separately recovered. The fraction comprising the aromatic feed substrate may be recycled in part to the alkylation reaction zone and in part to the transalkylation reaction zone. Normally, from about 25 wt.% to about 90 wt.%, and preferably from about 30 wt.% to about 85 wt.% of the aromatic substrate fraction is transported to the alkylation zone. The remainder of the aromatic feed substrate fraction and the entire dialkylated aromatic fraction are transported to the transalkylation reaction zone as the transalkylation reaction zone feed.

The transalkylation reaction zone accepts as feed the entire dialkylaromatic-rich fraction of the second separation zone and can accept as feed a portion of the aromatic substrate fraction recovered in the separation zone. A stream consisting of the aromatic substrate feed that has not been recovered in the separation zone but which has originated from a source outside of the process may be used as a portion of or all of the aromatic substrate feed being directed to the transalkylation reaction zone.

The dialkylaromatic stream that is utilized as a portion of the transalkylation reaction zone feed is comprised of aromatic compounds which are characterized as constituting an aromatic substrate based molecule with two olefin alkylating agent compounds taking the place of two hydrogen atoms around the aromatic substrate ring structure. The dialkylaromatic stream will also contain small amounts of aromatic compounds with boiling points similar to the dialkylaromatic such as hexylbenzene in the cumene production case.

The transalkylation reaction zone is utilized to remove the olefin alkylating agent compounds in excess of one from the ring structure of the dialkylated aromatic compounds and to transfer the removed alkylating agent compound to an aromatic substrate molecule that has not been previously alkylated, thus increasing the amount of monoalkylated aromatic compounds produced by the process. To transalkylate dialkylaromatics with an aromatic substrate, a feed mixture containing an aromatic substrate and the dialkylated aromatic compound in mole ratios ranging from 1:1 to 50:1 and preferably from 4:1 to 10:1 are continuously or intermittently introduced into a transalkylation reaction zone containing a transalkylation catalyst at transalkylation conditions. The transalkylation catalyst that is utilized in the transalkylation reaction zone of the present invention is a crystalline aluminosillicate material bound with a refractory inorganic oxide material.

The crystalline aluminosilicate material of the transalkylation catalyst of the present invention is a silica-alumina material having either a three-dimensional or channel-pore structure crystal lattice framework. The three-dimensional aluminosilicates include both synthetic and naturally occurring silica-aluminas, such as, the faujasites which include X-type, Y-type, ultrastable-Y and the like. L-type, omega-type, and mordenite are examples of the channel-pore structure crystalline aluminosilicates.

The aluminosilicate material that is preferred in the catalytic composition of this invention is the particular form of aluminosilicate material known as mordenite. While mordenite is naturally occurring, a variety of synthetic mordenities are available commercially, usually in powder form. These synthetic mordenities can be obtained in both the sodium form and hydrogen form and at varied silica to alumina ratios. It is a preferred embodiment of the present invention that the mordenite be of the hydrogen form and that the silica to alumina ratio be at least 8:1, more specifically, in the range from 8:1 to 25:1.

The hydrogen form aluminosilicate is incorporated with a refractory inorganic oxide and formed into a catalyst composite. The formed catalyst composite may be prepared by any known method in the art including the well-known oil drop and extrusion methods. The hydrogen form aluminosilicate may be present in an amount within the range of 5 to about 99.5 wt.%, preferably within the range of 60 to about 95 wt.%, and the refractory inorganic oxide may be present in an amount within the range of from 0.5 to about 95 wt.%. The preferred aluminosilicate may be modified by any method known in the art before, during, or after fabrication into a catalyst particle. Examples of potential modifications include steam deactivation, ion exchange to reduce the aluminosilicate to hydrogen form, the addition of metal modifiers, or other chemical modifiers, precoking, and so on.

The preferred inorganic oxide for use in the transalkylation catalyst of the present invention is alumina. The alumina is preferably selected from the group consisting of gamma-alumina, eta-alumina, and mixtures thereof. Other refractory inorganic oxides which are contemplated include, for example, silica gel, silica-alumina, magnesia-alumina, zirconia-alumina, aluminum phosphates, and the like.

It has been found that a strong correlation exists between the transalkylation performance of a catalyst composite of the subject invention and the surface area of said composite. To achieve maximum transalkylation catalyst performance the formed catalytic composite should have the highest possible surface area. Surface area, as referred to herein, is determined by employing the Langmuir method of correlating adsorption/desorption isotherm data. The Langmuir method is especially suitable for catalytic composites containing high percentages of crystalline aluminosilicates, whereas other calculation methods are used primarily for determining surface areas of amorphous, less defined solids. The data needed for the Langmuir method is typically obtained by well-known adsorption/desorption apparatus, preferably a nitrogen adsorption/desorption apparatus. Catalytic composites with high surface areas can be arrived at in a number of ways, such as, using a crystalline aluminosilicate powder which inherently has a very high surface area, or by having one component of the composite, which has a high surface area, in great proportion to other components.

In a continuous process comprising in part a transalkylation zone for the transalkylation of dialkylaromatic compounds with an aromatic substrate, the above-described transalkylation reactants are fed in admixture into a pressure vessel containing the above-described crystalline aluminosilicate transalkylation catalyst. The transalkylation catalyst may be contained in one bed within a reactor vessel or divided up among a plurality of beds within a reactor. The alkylation reaction system may contain one or more reaction vessels in series. The feed to the transalkylation reaction zone can flow vertically upwards, or downwards through the catalyst bed in a typical plug-flow reactor, or horizontally across the catalyst bed in a radial flow type reactor.

Temperatures which are suitable for use in the process herein are those temperatures which initiate a reaction between an aromatic substrate compound and the dialkylaromatic compounds recovered in the first and second separation sections to selectively product the desired monoalkylaromatic compound. Generally, temperatures suitable for promoting the transalkylation reactions are from about 100° C. to about 390° C., and especially from about 125° C. to about 275° C. Pressures which are suitable for use herein preferably are above about 1 atm but should not be in excess of about 130 atm. An especially desirable pressure range is from about 10 to about 40 atm. A liquid hourly space velocity (LHSV) of from about 0.1 to about 50 $hr^{-1}$, and especially from about 0.5 to about 5 $hr^{-1}$ based upon the combined aromatic substrate and dialkylaromatic feed rate is desirable. It should be noted that the temperature and pressure combination utilized in the transalkylation reaction zone is to be such that the transalkylation reactions take place in essentially the liquid phase. In a liquid phase transalkylation process for producing monoalkylaromatics, the catalyst is continuously washed with reactants, thus preventing buildup of coke precursors on the catalyst.

The practice of using only dialkylaromatic polyalkylated components as opposed to using di-, tri-, and tetraalkylated aromatics as a portion of the feed to the transalkylation reactor, like performing the reaction in the liquid phase, assists in minimizing coke accumulation on the transalkylation catalyst. It is suspected that if the trialkylaromatic and heavier aromatic components removed from the feed to the transalkylation reaction zone in the second separation zone of the instant invention were allowed to come into contact with the transalkylation catalyst, that they would accumulate in the pores of the catalyst and become unable to desorb at normal reactor operating conditions thus negating the catalytic activity of the plugged pores. This accumulation of heavy compounds in the transalkylation catalyst pores would then lead to a loss in catalytic activity. Thus, the use of only dialkylaromatic polyalkylated components as a portion of the transalkylation reaction zone feed, and the operation of the transalkylation reaction in the liquid phase results in reduced amounts of carbon forming on said catalyst in which case catalyst cycle life is extended as compared to a gas phase transalkylation process, and liquid phase transalkylation processes where trialkylaromatic and heavier compounds are transalkylated, in which cases, coke formation and catalyst deactivation is a major problem.

The transalkylation reaction zone catalyst as disclosed hereinabove has been found to be regenerable by exposing the deactivated transalkylation catalyst to a hot liquid benzene washing step. It is preferred that the hot benzene washing of a deactivated transalkylation catalyst occur at temperatures of 250° C. or greater. At temperatures above 250° C., the hot benzene has been found to be most effective in desorbing large aromatic molecules that plug and deactivate the catalyst pores of the transalkylation catalyst thus returning the transalkylation catalyst to an essentially fresh condition of activity. It is anticipated that the desired aromatic substrate and aromatic components other than the desired aromatic substrate can be equally effective in regenerating the transalkylation catalyst via hot hydrocarbon liquid washing. Benzene is disclosed as the preferred hydrocarbon component due to its probable availability in a process of the instant invention.

The transalkylation catalyst of this process may be regenerated at any time by halting the flow of all streams to the transalkylation reaction zone except for the aromatic substrate feed stream. As mentioned above, it is preferred that the aromatic substrate is benzene. It is also preferred that the catalyst is regenerated only after the transalkylation catalyst exhibits at least a 10% loss in dialkylated aromatic conversion. In this way, the frequency of catalyst regeneration cycles will be minimized. It is most preferred if the transalkylation catalyst is regenerated after exhibiting a dialkylated aromatic conversion drop of 25% or more in comparison to the fresh catalyst conversion value.

The transalkylation catalyst should be exposed only to the aromatic substrate under liquid phase conditions during the regeneration step. The regeneration step occurs at an elevated temperature of at least about 100° C. and preferably above about 250° C.

The transalkylation catalyst is contacted with the hot aromatic substrate at elevated conditions until essentially no catalyst deactivating material remains on the transalkylation catalyst. By "essentially all", it is meant that only small amounts or no heavy hydrocarbons responsible for the catalyst deactivation are detected either by sight, or by analysis such as liquid chromatography.

The aromatic substrate liquid useful in washing the deactivated transalkylation catalyst in order to reactivate it may be directed to the first separation zone in order to remove the heavy catalyst deactivating hydrocarbons from the wash liquid. This allows for the recycle of the aromatic substrate to the alkylation or transalkylation reactor.

During the regeneration of the transalkylation catalyst, the dialkylated aromatic-rich hydrocarbon fraction of the second separation zone is redirected from the transalkylation reaction zone to either the inlet of the alkylation reaction zone, or to storage for later processing. It is preferred that the stream is directed to the alkylation reaction zone.

The following examples are introduced to further describe the process of the invention. The examples are intended as illustrative embodiments and should not be considered to restrict the otherwise broad interpretation of the invention as set forth in the claims appended hereto.

EXAMPLE I

Catalyst A was formulated by a method consistent with that of the transalkylation catalyst of the present invention. The starting material for Catalyst A was the hydrogen form, low sodium, partially dealuminated synthetic mordenite powder (marketed by Union Carbide under the name LZ-M-8), hereinafter referred to as the as-received mordenite.

The as-received mordenite powder was mixed with an alumina powder to a weight ratio of 9:1, followed by the addition of an acidified peptization solution. The admixture was then extruded by means known in the art. After the extrusion process, the extrudate was dried and calcined.

Following the drying and calcination steps, the extrudate was washed in an aqueous solution comprising 10 wt.% HCl and 10 wt.% NH$_4$Cl at 60° C. for 150 minutes at a solution to zeolite volumetric ratio of 5:1. After the wash step, the catalyst was again dried and calcined. Catalyst A is a crystalline aluminosilicate transalkylation reaction zone catalyst of the present invention. The resulting surface area of the catalyst was 620 m$^2$/g.

EXAMPLE II

Transalkylation Catalyst A of the instant invention was tested in a pilot plant to determine catalyst stability over time while processing a feedstock produced from an SPA alkylation catalyst. During the stability testing, the deactivation of the instant transalkylation catalyst over time was compared when processing a feedstock comprising diisopropylbenzene and benzene obtained by fractionating the alkylation reaction zone heavy product in a second fractionation zone to obtain an essentially pure diisopropylbenzene feed stream as is done in the instant invention, and when processing a feedstock comprising diisopropylbenzene, benzene, and heavier and lighter aromatic compounds or in other words, the alkylation reaction zone heavy product. The pilot plant utilized in evaluating the catalyst stability of the instant transalkylation catalyst consisted of a tubular reactor holding 50 cc of transalkylation catalyst connected to a product recovery zone. The reactor pressure was maintained at 34 atm, the temperature at 150° C., and the combined liquid hourly space velocity at 1.3 hu$^{-1}$. A comparison of the effect of transalkylation feedstock composition on transalkylation catalyst deactivation can be found in the Table below. Case I represents the results of a diisopropylbenzene, benzene feedstock which corresponds to the transalkylation reaction zone feedstock of this invention, while Case II represents the results of processing a feedstock containing diisopropylbenzene and heavier and lighter aromatic compounds and benzene as is done in the prior art.

|  | Case I | Case II |
|---|---|---|
| Feedstock (weight %) | | |
| Cumene | 0.0 | 0.1 |
| Butyl-, Pentylbenzenes | 0.3 | 0.6 |
| DIPB | 20.0 | 21.1 |
| Hexylbenzenes | 4.8 | 6.0 |
| Heavy Aromatics | 0.0 | 1.1 |
| Benzene | 74.9 | 71.1 |
| Total | 100.0 | 100.0 |
| Benzene/DIPB Mole Ratio | 7.8/1 | 7.0/1 |
| Hours On-Stream | 360 | 100 |
| Initial DIPB Conversion | 50% | 35% |
| Final DIPB Conversion | 50% | 28% |
| Loss of DIPB Conversion | 0% | 7% |
| Rate of Loss of DIPB Conversion | 0%/100 hr | 7%/100 hr |

The results above indicate the dramatic effect that feedstock composition has upon the deactivation rate of a transalkylation catalyst of the instant invention. The deactivation rate of the instant transalkylation catalyst processing the benzene, dipropylbenzene feed in Case I is significantly slower than that for the same catalyst processing the heavy aromatic containing feedstock of Case II. As stated, the Case I feedstock represents the transalkylation reaction zone feedstock which emanates from the second separation zone of the instant process. The Case II feedstock represents the transalkylation reaction zone feedstock from an alkylation-transalkylation process without a second separation zone. Thus, the use of a second separation zone to separate substantially all of the heavier aromatic compounds and a portion of light aromatics from the diisopropylbenzene-rich fraction fed to the transalkylation reaction zone clearly and dramatically improves the active life of a transalkylation catalyst.

EXAMPLE III

This example provides evidence regarding the regenerability of the instant transalkylation catalyst. After 1200 hours on-stream in a pilot plant at conditions identical to those disclosed in Example V, Case I, a transalkylation catalyst of the instant invention was exhibiting a diisopropylbenzene conversion of about 30%. This was well below the fresh catalyst diisopropylbenzene conversion value of 49–50%. The deactivated transalkylation catalyst was then regenerated with a hot benzene wash step. The hot benzene transalkylation catalyst regeneration step was accomplished by:

taking the transalkylation reactor out of service,
flushing the reactor with benzene at an LHSV of 1.3 hr$^{-1}$ over 12 hours,
raising reactor temperature from 150° C. to 250° C., then holding the reactor at 250° C. for 12 hours and maintaining a once-through benzene rate corresponding to an LHSV of 1.3 hr$^{-1}$,
reducing the reactor temperature from 250° C. to 150° C. over 12 hours at a once-through benzene space velocity of 1.3 hr$^{-1}$, and
putting the transalkylation reactor back in service.

After the transalkylation catalyst regeneration procedure was completed and the reactor placed back in service, the transalkylation catalyst diisopropylbenzene conversion had improved to a value of 51%. This example demonstrates the utility of the use of a hot benzene wash step to restore the activity of a previously deactivated transalkylation catalyst of the instant invention. The example also obviously demonstrates the regenerability of the instant acid-washed transalkylation catalyst.

What is claimed is:

1. A process for the production of alkylated aromatics and containing a regenerable transalkylation catalyst which comprises the steps of:

(a) passing a feedstream comprising an alkylating agent and an aromatic substrate to an alkylation reaction zone and into contact with a solid phosphoric acid containing catalyst under conditions providing for the liquid phase alkylation of said aromatic substrate;

(b) separating in a first separation zone the product from the alkylation reaction zone and a hereinafter described transalkylation reaction zone product into fractions comprising (1) an aromatic substrate fraction, (2) a substantially pure monoalkylated aromatic fraction, and (3) a fraction comprising compounds with boiling points higher than the desired monoalkylated aromatic;

(c) separating in a second separation zone the fraction comprising compounds with boiling points higher than the desired monoalkylated aromatic of the first separation zone into a dialkylated aromatic-rich fraction, and into fractions with higher and lower boiling points than the dialkylated aromatic-rich fraction;

(d) passing a feed stream of an aromatic substrate and the separated dialkylated aromatic-rich hydrocarbon fraction of the second separation zone to a transalkylation reaction zone containing crystalline aluminosilicate catalyst under conditions providing for the transalkylation of said dialkylated aromatic-rich hydrocarbon fraction to produce a transalkylation reaction zone product;

(e) introducing the transalkylation reaction zone product from step (d) into the separation zone of step (b);

(f) recovering the monoalkylaromatic fraction; and (g) intermittently halting the flow of the separated dialkylated aromatic-rich hydrocarbon fraction of the second separation zone to the transalkylation reaction step (d) and thereby allowing only the aromatic substrate to contact and regenerate the crystalline aluminosilicate transalkylation catalyst until essentially no catalyst deactivating material remains on the catalyst and thereafter resuming the flow of the separated dialkylated aromatic-rich hydrocarbon fraction to the transalkylation reaction step.

2. The process defined in claim 1 wherein at least a portion of the separated aromatic substrate fraction of step (b) is recycled to the alkylation reaction zone.

3. The process defined in claim 1 wherein at least a portion of the separated aromatic substrate fraction of step (b) is recycled to the transalkylation reaction zone.

4. The process defined in claim 1 wherein the dialkylated aromatic-rich hydrocarbon fraction of the second separation zone is directed to the alkylation reaction zone when it is halted from flowing to the transalkylation reaction zone during transalkylation catalyst regeneration.

5. The process defined in claim 1 wherein the dialkylated aromatic-rich hydrocarbon fraction of the second separation zone is directed to storage when it is halted from flowing to the transalkylation reaction zone during transalkylation catalyst regeneration.

6. A process containing a regenerable transalkylation catalyst useful in the liquid phase production of a monoalkylbenzene which comprises the steps of:
   (a) reacting a $C_2$-$C_{14}$ monoolefin alkylating agent with benzene in the presence of a solid phosphoric acid containing alkylation catalyst under conditions providing for the liquid phase alkylation of said benzene;
   (b) separating in a first separation zone said alkylation reaction zone effluent stream, a transalkylation reaction zone effluent stream as hereinafter characterized, and a benzene containing feed stream into (1) a benzene-rich feed fraction, (2) a substantially pure monoalkylbenzene product fraction, and (3) a fraction rich in compounds with boiling points higher than the desired monoalkylbenzene;
   (c) separating in a second separation zone the fraction rich in compounds with boiling points higher than the desired monoalkylbenzene of the first separation zone into a dialkylbenzene-rich fraction, and into fractions with higher and lower boiling points than the dialkylbenzene-rich fraction;
   (d) transalkylating the dialkylbenzene-rich fraction with a first portion of the separated benzene-rich feed fraction in the presence of a transalkylation reaction zone catalyst comprising an inorganic oxide-bound crystalline aluminosilicate material in a transalkylation reaction zone under transalkylation reaction conditions to produce a transalkylation reaction zone effluent stream;
   (e) supplying the effluent of the transalkylation reaction zone to said first separation zone as said transalkylation reaction zone effluent stream;
   (f) passing a second portion of said unreacted benzene-rich feed fraction to said alkylation reaction zone as a portion of the alkylation reaction zone feed;
   (g) recovering said monoalkylbenzene product fraction from the separation zone; and
   (h) regenerating the transalkylation catalyst when the transalkylation catalyst dialkylaromatic conversion performance is at least 10 percent below that of the fresh transalkylation catalyst dialkylaromatic conversion performance by:
      (i) directing the flow of the separated dialkylated aromatic-rich hydrocarbon fraction to storage or to the alkylation reaction zone,
      (ii) contacting the transalkylation catalyst with the separated benzene-rich feed fraction of step (d) at a temperature of at least 100° C. until essentially no catalyst deactivating material remains on the transalkylation catalyst; and
      (iii) resuming the flow of the separated dialkylated aromatic-rich hydrocarbon fraction of the second separation zone to the transalkylation reaction zone under transalkylation reaction conditions.

7. The process defined in claim 6 wherein the transalkyaltion reaction zone catalyst is comprised of from 5% to 99.5% by weight of a crystalline aluminosilicate material which is characterized as having an average pore diameter of 6 angstroms or greater.

8. The process defined in claim 7 wherein the transalkylation reaction zone catalyst is comprised of from 5% to 95% by weight of an inorganic oxide support selected from the group consisting of $Al_2O_3$, $SiO_2$, $AlPO_4$, and mixture thereof.

9. The process defined in claim 8 wherein the crystalline aluminosilicate material contained in the transalkylation reaction zone catalyst is mordenite.

10. The process defined in claim 6 wherein the monoolefin alkylating agent is ethylene.

11. The process defined in claim 6 wherein the monoolefin alkylating agent is propylene.

12. The process defined in claim 6 wherein the monoolefin alkylating agent comprises a $C_9$-$C_{14}$ olefin.

13. A process containing a regenerable transalkylation catalyst useful in the liquid phase production of cumene which comprises the steps of:
   (a) reacting propylene with benzene in the presence of a solid phosphoric acid containing alkylation catalyst in an alkylation reaction zone operating at a temperature of from 100°-390° C., a pressure of from 1-130 atmospheres, a liquid hourly space velocity of from 0.5 to 50 hr$^{-1}$, and a benzene to propylene molar feed ratio of from 1:1 to 20:1;
   (b) passing the alkylation reaction zone effluent stream, the transalkylation reaction zone effluent stream as hereinafter characterized, and a benzene containing feed stream into a first separation zone wherein entering hydrocarbons are separated into an unreacted benzene-rich feed fraction, a substantially pure cumene and product fraction, and a fraction rich in compounds with boiling points higher than cumene;
   (c) separating in a second separation zone the fraction rich in compounds with boiling points higher than cumene of the first fractionation zone into a diisopropylbenzene-rich fraction and into fractions with boiling points higher and lower than that of the dipropylbenzene-rich fraction;
   (c) transalkylating the diisopropylbenzene fraction with a first portion of the separated benzene-rich feed fraction in the presence of a transalkylation reaction zone catalyst comprising from 5% to 95% by weight of mordenite, from 5% to 95% by weight of $Al_2O_3$, at a transalkylation reaction zone temperature of from 100° C. to 390° C., a pressure of from 1 to 130 atmospheres, a liquid hourly space velocity of from 0.1 to 50 hr−1 and a benzene to diisopropylbenzene molar feed ratio of from 1:1 to 1:20 to produce a transalkylation reaction zone effluent stream;
   (e) supplying the effluent stream of the transalkylation reaction zone to said first separation zone as said transalkylation reaction zone effluent stream;
   (f) passing a second portion of said unreacted benzene-rich feed fraction to said alkylation reaction zone as a portion of the alkylation reaction zone feed;
   (g) recovering said cumene product fraction from the separation zone; and
   (h) regenerating the transalkylation catalyst when the diisopropylbenzene conversion across the transalkylation catalyst is at least 25 percent below that of the fresh catalyst diisopropylbenzene conversion performance by:
      (i) directing the flow of the diisopropylbenzene-rich fraction of the second separation zone to the inlet of the alkylation reaction zone;
      (ii) contacting the transalkylation catalyst with the first portion of the separated benzene-rich fraction in the liquid phase and at a temperature of at least 250° C. until essentially no catalyst reactivating material remains on the transalkylation catalyst; and
      (iii) directing the flow of the diisopropylbenzene-rich fraction of the second separation zone to the transalkylation reaction zone.

* * * * *